(12) United States Patent
Axon et al.

(10) Patent No.: US 9,808,142 B2
(45) Date of Patent: Nov. 7, 2017

(54) COVERING FOR A MEDICAL SCOPING DEVICE

(75) Inventors: Anthony Axon, Leeds (GB); Patrick Axon, Leeds (GB)

(73) Assignee: Arc Medical Design Limited, Leeds (GB)

( * ) Notice: Subject to any disclaimer, the term of this patent is extended or adjusted under 35 U.S.C. 154(b) by 92 days.

(21) Appl. No.: 13/699,172

(22) PCT Filed: May 24, 2011

(86) PCT No.: PCT/GB2011/050981
§ 371 (c)(1),
(2), (4) Date: Nov. 20, 2012

(87) PCT Pub. No.: WO2011/148172
PCT Pub. Date: Dec. 1, 2011

(65) Prior Publication Data
US 2013/0090527 A1    Apr. 11, 2013

(30) Foreign Application Priority Data

May 25, 2010  (GB) .................................. 1008637.9
Jan. 31, 2011  (GB) .................................. 1101619.3
May 6, 2011   (GB) .................................. 1107535.5

(51) Int. Cl.
*A61B 1/00*   (2006.01)
*A61M 29/00*  (2006.01)
(Continued)

(52) U.S. Cl.
CPC ........ *A61B 1/00135* (2013.01); *A61B 1/0008* (2013.01); *A61B 1/00075* (2013.01);
(Continued)

(58) Field of Classification Search
CPC ........... A61B 1/00094; A61B 1/00075; A61B 1/0008; A61B 1/00135; A61B 1/00137;
(Continued)

(56) References Cited

U.S. PATENT DOCUMENTS 3,717,151 A * 2/1973 Collett .............. A61M 25/0606
                                                         604/106
4,207,872 A    6/1980 Meiri et al.
(Continued)

FOREIGN PATENT DOCUMENTS

CN    101116607 A    7/2010
DE    10027447 A1    2/2001
(Continued)

OTHER PUBLICATIONS

Office Action corresponding to Chinese Application No. 201180026078.5 dated Sep. 2, 2014.
(Continued)

*Primary Examiner* — Timothy J Neal
*Assistant Examiner* — Aaron B Fairchild
(74) *Attorney, Agent, or Firm* — Myers Bigel, P.A.

(57) ABSTRACT

The present invention relates to a cover having a plurality of moveable, external, angled projecting elements for use with flexible medical scoping devices such as endoscopesor enteroscopes. The invention includes the cover with an over cuff and use of the disposable removable covering in methods of medical scoping procedures or examinations. The invention also includes an applicator for assisting in placing the covering about or over a medical device and a kit of parts.

9 Claims, 9 Drawing Sheets

(51) Int. Cl.
*A61B 1/31* (2006.01)
*A61B 1/32* (2006.01)
*A61B 1/015* (2006.01)
*A61B 1/01* (2006.01)
*A61M 25/04* (2006.01)
*A61M 25/00* (2006.01)

(52) U.S. Cl.
CPC ...... *A61B 1/00137* (2013.01); *A61B 1/00142* (2013.01); *A61B 1/00147* (2013.01); *A61B 1/00154* (2013.01); *A61B 1/01* (2013.01); *A61B 1/015* (2013.01); *A61B 1/31* (2013.01); *A61B 1/32* (2013.01); *A61M 25/04* (2013.01); *A61M 29/00* (2013.01); *A61M 2025/006* (2013.01)

(58) Field of Classification Search
CPC . A61B 1/00142; A61B 1/00147; A61B 1/015; A61B 1/32; A61B 1/00154; A61B 1/00087; A61B 1/00149; A61B 1/31; A61B 1/00089; A61B 1/00101; A61M 2025/006; A61M 25/0074; A61M 25/01; A61M 25/013; A61M 25/04; A61M 25/10
USPC .............................. 600/114, 153, 127, 129
See application file for complete search history.

(56) References Cited

U.S. PATENT DOCUMENTS

| | | | | |
|---|---|---|---|---|
| 5,018,509 | A | * | 5/1991 | Suzuki et al. ............... 600/115 |
| 5,505,686 | A | | 4/1996 | Willis et al. |
| 5,653,690 | A | * | 8/1997 | Booth et al. ............ 604/103.07 |
| 5,707,342 | A | | 1/1998 | Tanaka |
| 5,817,062 | A | | 10/1998 | Flom et al. |
| 5,916,145 | A | | 6/1999 | Chu et al. |
| 6,293,907 | B1 | | 9/2001 | Axon et al. |
| 6,416,462 | B1 | | 7/2002 | Tovey et al. |
| 6,589,213 | B2 | | 7/2003 | Reydel |
| 2002/0183593 | A1 | | 12/2002 | Chin et al. |
| 2003/0040685 | A1 | | 2/2003 | Lewkowicz et al. |
| 2003/0074015 | A1 | | 4/2003 | Nakao |
| 2003/0092964 | A1 | | 5/2003 | Kim et al. |
| 2003/0233025 | A1 | | 12/2003 | Saadat et al. |
| 2004/0073088 | A1 | | 4/2004 | Friedman et al. |
| 2004/0073089 | A1 | | 4/2004 | Nozue |
| 2004/0077926 | A1 | | 4/2004 | Moriyama |
| 2004/0097788 | A1 | | 5/2004 | Mourlas et al. |
| 2004/0102681 | A1 | | 5/2004 | Gross |
| 2004/0210116 | A1 | | 10/2004 | Nakao |
| 2005/0049624 | A1 | | 3/2005 | Francese et al. |
| 2005/0165273 | A1 | | 7/2005 | Takano |
| 2005/0165281 | A1 | | 7/2005 | Ravikumar et al. |
| 2006/0025653 | A1 | | 2/2006 | Bachler et al. |
| 2006/0258909 | A1 | | 11/2006 | Saadat et al. |
| 2007/0015965 | A1 | * | 1/2007 | Cox .................. A61B 1/00082 600/114 |
| 2007/0123798 | A1 | | 5/2007 | Rahamimov |
| 2007/0149845 | A1 | | 6/2007 | Kuhns et al. |
| 2007/0149850 | A1 | | 6/2007 | Spivey et al. |
| 2007/0167679 | A1 | | 7/2007 | Miyamoto et al. |
| 2007/0282255 | A1 | | 12/2007 | Salemi et al. |
| 2008/0058590 | A1 | | 3/2008 | Saadat et al. |
| 2008/0135053 | A1 | | 6/2008 | Gruber et al. |
| 2008/0215036 | A1 | | 9/2008 | Vogel et al. |
| 2009/0048483 | A1 | | 2/2009 | Yamamoto |
| 2009/0137867 | A1 | | 5/2009 | Goto |
| 2009/0149716 | A1 | | 6/2009 | Diao et al. |
| 2009/0281374 | A1 | | 11/2009 | Leanna et al. |
| 2009/0287052 | A1 | | 11/2009 | Amos et al. |
| 2009/0306472 | A1 | | 12/2009 | Filipi et al. |
| 2010/0010310 | A1 | | 1/2010 | Weisenburgh, II et al. |
| 2010/0081877 | A1 | | 4/2010 | Vakharia |
| 2010/0198012 | A1 | | 8/2010 | Poole et al. |
| 2011/0004058 | A1 | | 1/2011 | Oneda et al. |
| 2011/0009696 | A1 | | 1/2011 | Miyoshi |
| 2011/0282353 | A1 | | 11/2011 | McHugo |
| 2012/0197083 | A1 | | 8/2012 | Spenser |
| 2012/0302944 | A1 | | 11/2012 | Costovici |
| 2013/0035552 | A1 | | 2/2013 | Moriyama |
| 2013/0237817 | A1 | | 9/2013 | Mihaljevic et al. |
| 2013/0281784 | A1 | | 10/2013 | Ray |
| 2014/0046139 | A1 | | 2/2014 | Cole et al. |
| 2014/0094655 | A1 | | 4/2014 | Newman |
| 2014/0187939 | A1 | | 7/2014 | Ogawa |
| 2014/0207150 | A1 | | 7/2014 | Rosa et al. |
| 2014/0350461 | A1 | | 11/2014 | Nishiie |

FOREIGN PATENT DOCUMENTS

| | | | | |
|---|---|---|---|---|
| ES | 1051891 | U | | 10/2002 |
| JP | H0777576 | | * | 8/1995 ......... A61B 1/00082 |
| JP | 2003-33319 | A | | 2/2003 |
| JP | 2003033319 | | * | 2/2003 ......... A61B 1/00147 |
| JP | 2003180611 | A | | 7/2003 |
| JP | 2003-339631 | A | | 12/2003 |
| JP | 2003339631 | | * | 12/2003 ......... A61B 1/00147 |
| JP | 2006026344 | A | | 7/2004 |
| JP | 4804664 | B2 | | 11/2011 |
| WO | WO 98/47422 | A2 | | 10/1998 |
| WO | WO 99/29362 | A1 | | 6/1999 |
| WO | WO 97/43941 | A1 | | 11/1999 |
| WO | WO 00/13736 | A1 | | 3/2000 |
| WO | WO 2004/019769 | A1 | | 3/2004 |
| WO | WO 2006/138409 | A2 | | 12/2006 |
| WO | WO 2007/103999 | A1 | | 9/2007 |
| WO | WO 2011/019388 | A2 | | 2/2011 |
| WO | WO 2011/039756 | A1 | | 4/2011 |
| WO | WO 2013/132861 | A1 | | 12/2013 |
| WO | WO 2013/190543 | A1 | | 12/2013 |
| WO | WO 2014/045980 | A1 | | 3/2014 |
| WO | WO 2014/123563 | A1 | | 8/2014 |
| WO | WO 2014/174950 | A1 | | 10/2014 |

OTHER PUBLICATIONS

Invitation to Respond to Written Opinion corresponding to Singapore Application No. 201208472-9 dated Feb. 11, 2014.
International Search Report corresponding to PCT/GB2011/050981 dated Dec. 27, 2011.
Written Opinion of the International Preliminary Examining Authority corresponding to PCT/GB2011/050981 dated Jun. 12, 2012.
Notification of Transmittal of the International Preliminary Report on Patentability corresponding to PCT/GB2011/050981 dated Oct. 1, 2012.
Search Report corresponding to GB 1008637.9 dated Aug. 31, 2010.
Combined Search and Examination Report corresponding to GB 1108723.6 dated Jun. 9, 2011.
EP Community Design Certificate of Registration No. 001856121-0001 registered Apr. 27, 2011.
EP Community Design Certificate of Registration No. 002523191-0001 registered Aug. 21, 2014.
European Search Report corresponding to European Application No. 15169674.7 dated Sep. 1, 2015.
Notice of Opposition corresponding to European Application No. 11722861.9 dated Sep. 21, 2016.
EPO Communication corresponding to European Application No. 11722861 9 dated Nov. 2, 2016 (2 pages).
Application No. GB 1008637.9, filed May 25, 2010.
Application No. GB 1101619.3; flied Jan. 31, 2011.
Application No. GB 1107535.5; filed May 6, 2011.
Opposition Statement corresponding to Opposition Proceedings against European Patent No. 2575590 (39 pages) (dated Sep. 14, 2016).
Opposition Reply corresponding to Opposition Proceedings against European Patent No. 2575590 (5 pages) (dated Mar. 13, 2017).
Opposition Preliminary Opinion from the European Patent Office corresponding to Opposition Proceedings against European Patent No. 2575590 (4 pages) (dated May 4, 2017).

(56) References Cited

OTHER PUBLICATIONS

Court Pleadings filed in the United Kingdom against counterpart European Patent No. 2575590 and United Kingdom Patent No. 2478081 (4 pages) (dated May 30, 2017).
Claim form corresponding to UK Patent No. 2478081 and European Patent No. 2575590 dated Sep. 23, 2016 (2 pages).
Defence and Counterclaim corresponding to UK Patent No. 2478081 and European Patent No. 2575590 dated Nov. 15, 2016 (10 pages).
Grounds of Invalidity corresponding to UK Patent No. 2478081 and European Patent No. 2575590 dated Sep. 26, 2016 (4 pages).
Particulars of Claim corresponding to UK Patent No. 2478081 and European Patent No. 2575590 dated Sep. 26, 2016 (3 pages).

\* cited by examiner

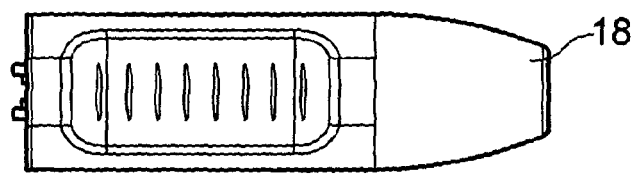
FIG. 6A
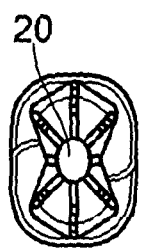
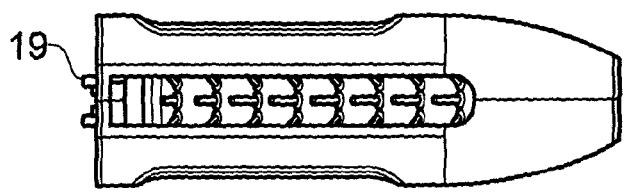
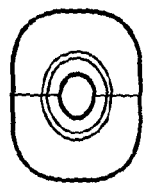
FIG. 6D          FIG. 6B          FIG. 6E
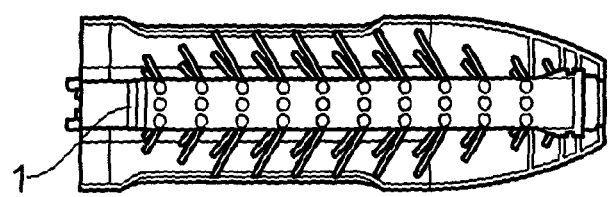
FIG. 6C
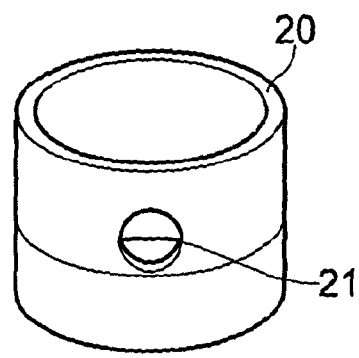
FIG. 7

COVERING FOR A MEDICAL SCOPING DEVICE

RELATED APPLICATIONS

This application is a 35 U.S.C. §371 national stage application of PCT Application No. PCT/GB2011/050981, filed on May 24, 2011, which claims priority from British Application No. 1107535.5, filed on May 6, 2011, British Application No. 1101619.3, filed on Jan. 31, 2011, and British Application No. 1008637.9 filed on May 25, 2010. The contents of each of these applications are incorporated herein by reference in their entireties. The above-referenced PCT International Application was published as International Publication No. WO 2011/148172 A2 on Dec. 1, 2011.

The present invention relates to a covering or sheath or sleeve or cuff having external projections for use with a medical device and in particular for use with flexible medical scoping devices such as endoscopes or enteroscopes. The invention includes inter alia use of the disposable removable covering in methods of medical scoping procedures or examinations, particularly but not exclusively, where the site is the colon or small intestine. The invention also includes a kit including an applicator for assisting in placing the covering about or over a medical scoping device.

BACKGROUND

In endoscopic examinations/procedures, flexible instruments designed to view the gastro-intestinal tract are inserted along a body cavity to an internal part such as the stomach, duodenum, small intestine or large intestine. The instruments are provided with fibre-optic or charge-couple device (CCD) cameras which enable images to be transmitted around bends and images to be produced to displays on a television screen. Accordingly, it is possible to view the inside surfaces of the oesophagus, stomach and duodenum using a gastroscope, the small intestine with an enteroscope, part of the colon using a flexible sigmoidoscope and the whole of the large intestine (the bowel) with a colonoscope.

Enteroscopy is the endoscopic examination of the small intestine whereas colonoscopy is the endoscopic examination of the colon and the distal part of the small bowel and flexible sigmoidoscopy is the examination of the rectum and lower part of the bowel. Each scoping procedure may provide a visual diagnosis (e.g. ulceration, polyps) and grants the opportunity for biopsy or removal of suspected lesions. Whilst colonoscopic and enteroscopic examinations are the most effective techniques to assess the state of health of the bowel, they are inconvenient, uncomfortable, expensive procedures that are associated with significant risks of potentially serious complications. The most common complications are: failure to achieve a complete examination (5-10%); failure to detect a polyp (up to 20%); reaction to intravenous drugs; over-sedation leading to hypoxia and cardio-vascular collapse; splenic injury (rare); bowel perforation, (1 in 500-1500); full thickness burn (uncommon) and; bleeding following polypectomy.

A further disadvantage of colonoscopic and enteroscopic procedures is that they are time consuming for patients and medical personnel alike, the procedure can take anywhere from 20 minutes to 2 hours depending on how difficult it is to advance a scope through the colon or small intestine. The colonoscopy itself takes around thirty minutes to perform but in some cases may require up to an hour, and for the patient, there is a recovery period of up to two hours in hospital whilst sedation passes off and over that time clinical observation is needed. Typically, the number of clinically competent personnel required to conduct a colonoscopic procedure are an endoscopist specialist and three assistants including the person responsible for reprocessing the equipment. In addition, staffing is required for the recovery area.

Two yet further additional significant difficulties associated with colonoscopy and scoping procedures more generally are as follows:

Firstly, the anatomy of the colon is such that the lining is thrown into folds. As the tip of the endoscope passes along the lumen of the colon, these folds hamper the endoscopist's ability to visualise the entire surface of the mucosa and in particular, detect pre-malignant and malignant lesions tucked away on the proximal face of these folds during extubation.

Secondly, the position of the tip of may be difficult to maintain from the moment at which a lesion or polyp is detected to the completion of any therapeutic procedure. As the colonoscope is withdrawn the tip does not travel back at a constant speed but rather with jerks and slippages particularly when traversing a bend or length of colon where the bowel has been concertinaed over the endoscope shaft during intubation. The tip of the device may, at any moment, slip backwards thereby causing the clinician to lose position. If tip position is lost, the clinician is required to relocate the lesion or polyp for the therapeutic procedure to be continued.

The colonoscopic procedure is not simple because the bowel is long and convoluted. In places it is tethered by peritoneal bands and in others it lies relatively free. When the tip of the endoscope encounters a tight bend the free part of the colon "loops" as more of the endoscope is introduced and so looping occurs in the free part of the colon before the bend when there is difficulty negotiating the bend. This leads to stretching of the mesentery of the loop (the tissue that carries the nerves and blood vessels to the bowel). If the stretching is continued or severe while the endoscopist pushes round the bend, the patient experiences pain the blood pressure falls and the pulse slows. Loop formation is the main cause of failure or delay in completing an examination. It is responsible for the pain experienced by the patient and the need for heavy sedation that in turn leads to cardio-respiratory complications. It is also the major cause of perforation in patients not undergoing a therapeutic procedure.

Attempts have been made to try to overcome the problems associated with colonoscopic procedures, for example, it is known in the prior art to provide endoscope sheaths having differential frictional resistance provided by very small external protrusions such as wedge-shaped profiles or scales so there is low frictional resistance during forward movement of the covered endoscope shaft through a body cavity and a greater frictional resistance during its rearward movement. In practice however little improvement is achieved in overcoming looping. It is also known from the prior art to use a double balloon enteroscope or an Aer-O-Scope™. The double balloon enteroscope requires a substantial amount of additional kit, a high level of operator skill in timing the sequential inflation and deflation of the balloons and moreover it is a lengthy procedure sometimes taking hours. The Aer-O-Scope™ provides low pressure colon insufflations with $CO_2$ to propel the balloon along "slippery" colon walls without forceful maneuvering but cannot be used for biopsy or therapy.

Despite the forgoing drawbacks, for the foreseeable future colonoscopy will remain the procedure of choice for the examination of the large bowel. Newer methods for the detection of polyps and cancer using non-invasive technology may be identified but to obtain biopsies, remove polyps and to treat intra-colonic lesions no alternatives have appeared to date.

An improved medical scoping device that could reduce the time taken for the colonoscopist or enteroscopist to perform the procedure would offer immediate advantages to patients and clinicians alike.

An improved medical scoping device that could reduce the risk of complications during a procedure would offer immediate advantages to patients and clinicians alike.

A medical scoping device that could improve endoscopic intubation, extubation and visualisation of the large bowel would offer immediate advantages to both patients and clinicians alike.

A medical scoping device that could reduce loss of tip position during a medical procedure would offer immediate advantages to both patients and clinicians alike.

An improved medical scoping device that could reduce the requirement or level of sedation for a patient would offer immediate advantages to both patients and clinicians alike.

An improved medical scoping device that could overcome the problems associated with looping and so reduce discomfort to the person on whom the procedure was being performed, would offer immediate advantages to patients and clinicians alike.

BRIEF SUMMARY OF THE DISCLOSURE

According to a first aspect of the present invention there is provided a cover for a medical scoping device shaft, the cover comprising an elongate tubular member and being arranged for application over the medical scoping device shaft with the cover extending along at least a part of the length of a distal end of the shaft, the tubular member comprising an inner surface at least a part of which grips the shaft and acts to hold the cover in place and an outer surface comprising a plurality of spaced projecting elements having a tip and a base that are moveable between a resting position to a position wherein the tip of the projecting element is substantially parallel to a longitudinal axis of the medical scoping device and to a position that is at an angle that is approximately perpendicular to the longitudinal axis of the medical scoping device shaft so that the said projecting elements are fanned out to contact with and provide support for and to dilate a lumen wall of a body passage into which the medical scoping device has been inserted.

According to a second aspect of the invention there is provided a medical scoping device comprising an air suction means for removing air from a body passage, an elongate flexible shaft having a proximal end associated with a viewing means and a distal end, the medical scoping device further comprising the cover of the first aspect of the invention releasably attached thereto and covering at least a part of the shaft at its distal end.

According to a third aspect of the invention there is provided a cover according to a first aspect of the invention or a medical scoping device of the second aspect of the invention for use in a scoping procedure.

According to a fourth aspect of the invention there is provided an applicator for attaching a cover to a shaft of a medical scoping device, the applicator comprising a pair of complimentarily mated casings each sized and shaped so as to accommodate a cover for a medical scoping device therein, each casing further comprising an engaging means for releasably engaging the casings to one another and each casing comprising at least one securing means for securing a proximal end of the said cover thereto.

According to a fifth aspect of the invention there is provided a kit comprising at least one cover according to the first aspect of the invention and an applicator according to the fourth aspect of the invention, optionally the kit further includes a medical scoping device and/or a cutting means and/or a distal end cap.

According to a sixth aspect of the invention there is provided a method of avoiding looping in a medical scoping procedure, the method comprising inserting a medical scoping device shaft having an air suction means for removing air from a body passage into an orifice of an individual under investigation, the medical scoping device further comprising a cover releasably attached to the medical scoping device shaft and covering at least a part of the shaft at its distal end, wherein the cover comprises an elongate tubular member having an inner surface at least a part of which grips the shaft and acts to hold the cover in place and an outer surface comprising a plurality of spaced projecting elements, and wherein when advancing the medical scoping device into the patient's bowel or small intestine and the distal end encounters a bend or loop in the patient's bowel or small intestine, the medical scoping device is withdrawn towards its proximal end causing the projecting elements to splay or fan out and to dilate the lumen of the bowel or small intestine whilst holding the medical scoping device in position, if necessary air is then drawn out causing the body passage walls to collapse around and about the projecting elements thereby drawing the body passage wall into spaces between the projecting elements so said projecting elements engage with and grip the body passage wall, the medical scoping device is then further withdrawn towards the proximal end causing it to straighten and the body passage wall to concertina along the shaft of the scope proximal to the bend or loop whilst the lumen ahead of the distal end opens up, the medical scoping device is then advanced towards its distal end and the bend or loop is navigated.

According to a seventh aspect of the invention there is provided a method of improving endoscopic visualisation, the method essentially comprising the steps of the sixth aspect of the invention wherein the projecting elements open a lumen and evert thereby flattening colonic folds for inspection during withdrawal whereby visualisation is further enhanced as colonic folds revert to their normal anatomical position permitting light from the medical scoping device to play across the mucosa, thus enabling careful visualisation of the surface of the mucosa that was hitherto hidden or difficult to view.

According to an eighth aspect of the invention there is provided a method of maintaining tip position and improving tip control during an examination, the method essentially comprising the steps of the sixth aspect of the invention wherein the projecting elements maintain the medical scoping device tip in a central part of the bowel lumen as the device moves in a proximal direction thereby holding the mucosa to prevent the tip from flipping backwards so as to maintain position during therapy.

BRIEF DESCRIPTION OF THE DRAWINGS

Embodiments of the invention are further described hereinafter with reference to the accompanying drawings, in which:

FIG. 6A shows a top view of an applicator, FIG. 6B shows a side view, FIG. 6C shows a top view of a disassembled applicator and cover, FIG. 6D shows a proximal end view and FIG. 6E shows a distal end view.

FIG. 7 shows a side view of a viewing means attachment.

FIG. 10 shows an alternative embodiment of the cover of the invention.

FIG. 11 shows a series of different views of an alternative embodiment of the cover of present invention including an over cuff.

FIG. 12 shows a series of schematic anatomical through sections of a medical scoping device with a cover of the present invention including the over cuff, in the course of a medical scoping procedure.

DETAILED DESCRIPTION

Figure 1:
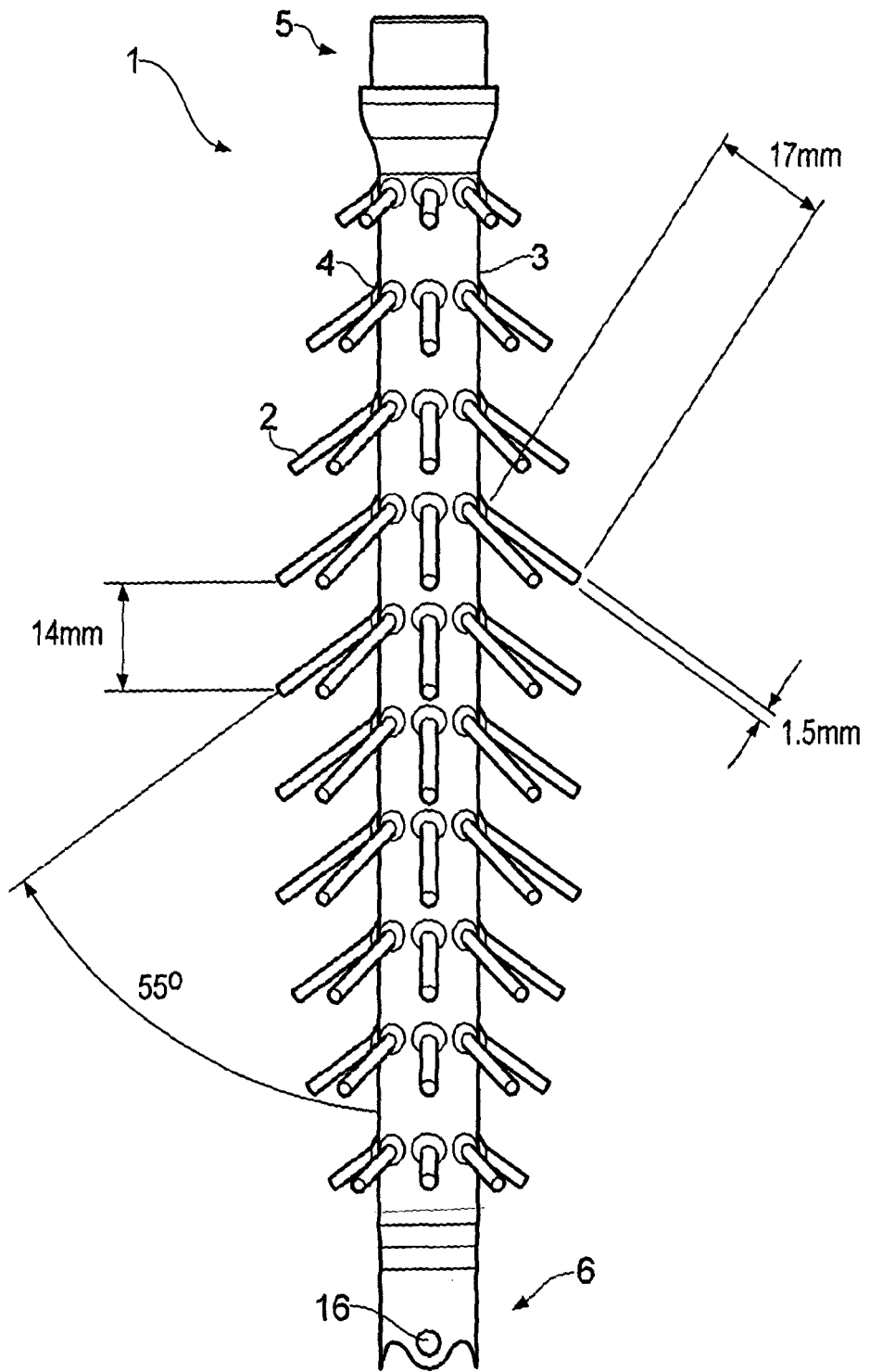
FIG. 1 shows one embodiment of the cover according to the present invention.

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

Reference herein to a "medical scoping device" is intended to refer to endoscopes, enteroscopes, sigmiodoscopes, gastroscopes, colonoscopes and panendoscopes and is used interchangeably and is intended to include all scoping instruments whether passed directly or through a cannula into a body/organ/tissue cavity. Endoscopy involves the inspection of the inside of the body or body cavity and includes arthroscopy, cystoscopy, gastroscopy, uteroscopy and colonoscopy whereas enteroscopy is the examination of the small intestine including the duodenum, jejunum, and ileum. In all instances the scopes are elongate flexible probes and it is intended that the covers of the present invention may be used in conjunction with all of the aforementioned scopes.

Accordingly a "medical scoping procedure" is intended to include any medical procedure or examination that involves use of a medical scoping device as hereinbefore described.

The distal end the cover is the end which is commensurate with the distal end of the medical scoping device shaft which comprises lenses, channels such as air suction conduits and light guides. It is the end which is furthest from the endoscopist/colonoscopist and as such is the end of the instrument which is deepest within the patient's body and therefore it is the end which will first come into contact with a looped segment of the bowel. Accordingly, a distal movement of the endoscope is a forward movement i.e. further into a patient's bowel. Conversely, the proximal end of the sheath is the end which is commensurate with the proximal end of the endoscope and which is the end situated nearest the operator and therefore a proximal movement of the endoscope is a backward movement towards the operator.

In one aspect of the present invention provides the medical scoping device cover provides an improved means of conducting probing procedures, avoiding the problems associated with looping and generally improving the speed and comfort of the procedure for the patient. The cover is arranged for application over the medical scoping device shaft so as to surround it and to extend along at least a distal part or tip region of the shaft. The cover comprises an inner surface at least a part of which grips the shaft of the medical device and holds the cover in place against movement longitudinally of the shaft during displacement of the shaft through a body passage into which the shaft is inserted in use, and the outer surface of the sleeve is provided with protrusions configured to cover the endoscope shaft onto which the cover is applied whereby the protrusions when fanned out or extended from the shaft body provide a means for gently holding on to or gripping the inner surface of the body passage and opening up the lumen. The gripping of the body passage by the projecting elements is enhanced by removal of any air in the body passage so that the wall of the body passage into which the medical device has been inserted collapses on to the projecting elements and is drawn into the spaces between the projecting elements thus the body passage walls are held against the cover and a rearward or proximal movement of the device causes the body passage to concertina behind the gripped portion of the body passage, the scope to straighten and the lumen ahead of the distal end to straighten and open up.

Preferably, the at least a part of an inner surface of the cover that is in contact with the distal end of the medical scoping device shaft may either be upper and lower end regions of the cover or the entire inner surface.

Preferably, the elongate tubular member may comprise a contiguous tubular member or alternatively it may be provided with slits or gaps or ridges running in a longitudinal direction commensurate with the longitudinal axis of the medical scoping device. In this embodiment of the invention the number of slits is directly proportional to the number of projecting elements, the projecting elements being positioned in the slits or gaps between the solid parts of the cover.

Preferably, the projecting elements are in the form of bristles, spikes, spines, fins, wedges, paddles or cones and are arranged to extend outwardly and away from the outer surface of the elongate tubular member. The projecting elements may be cylindrical, conical or tapered and the tips of the projecting elements may either be rounded or blunted.

Preferably, the projecting elements may be formed integrally with the outer surface of the elongate tubular member or alternatively they may be attached or moulded thereto. In the instance that the cover is provided with longitudinal slits or gaps then the projecting elements may be provided attached to or moulded in between adjacent slits or gaps.

In the instance of the projecting elements being attached or moulded to the outer surface of the cover, the bases of the projecting elements may be hinged onto the outer surface of the elongate tubular member. In this way the projecting elements are hinged and capable of moving between a resting position, where the tips extend away from the scoping device shaft at a selected angle, to a position wherein the tips of the projecting elements are substantially parallel to a longitudinal axis of the enteroscope/endoscope shaft and also to a position wherein the projecting elements project outwards from the enteroscope/endoscope shaft at an angle of less than or equal to perpendicular to the longitudinal axis of the medical scoping device shaft. In this position the projecting elements can be said to be fanned out.

In the alternative embodiment, the projecting elements are attached at their base to circumferentially positioned cross members situated below the level of the outer surface of the casing to form a hinge. In this way the projecting elements are hinged and capable of moving between a resting position, where the tips extend away from the scoping device shaft at a selected angle, to a position wherein the tips of the projecting elements are substantially parallel to a longitudinal axis of the enteroscope/endoscope shaft an fall below the level of the outer surface of the casing and also to a position wherein the projecting elements project outwards from the enteroscope/endoscope shaft at an angle of less than or equal to perpendicular to the longitudinal axis of the medical scoping device shaft. In this position the projecting elements can be said to be fanned out.

Preferably, the tips of the projecting elements when in a position of being substantially parallel to the longitudinal axis of the medical scoping device may either be directed towards a distal or proximal end of the covered medical scoping device. It will be appreciated that the projecting elements can be said to be moveable between at least three, and in some embodiments, four positions. In a first position the projecting elements project at a selected acute angle away from the longitudinal axis of the medical scoping device, this is the "resting position". In a second position when the covered medical scoping device is pushed in a distal direction into a patient's lumen forces act upon the projecting elements to push them towards the shaft of the scoping medical device so that they are substantially parallel to the longitudinal axis of the medical scoping device and so that the tips point towards a proximal end of the scope. In a third position, when the covered scoping device is withdrawn in a proximal direction the projecting elements are caused to fan out and are substantially perpendicular to the longitudinal axis of the shaft of the scoping medical device. In some embodiments of the invention the projecting elements are moveable beyond the third position and flick over at a critical point so that the tips point towards the distal end of the scoping medical device, this is the fourth position, and is the position in which the medical scoping device can be withdrawn through the orifice into which it was initially inserted. Alternatively, the cover may be provided with a projecting elements closure means optionally in the form of a sleeve which can be drawn from a distal to a proximal end and which flattens the projecting elements from the third or resting position to the second position described above.

Accordingly in some embodiments of the invention where the projecting elements do not flick over at a critical point the covers of the present invention are preferably provided with a projecting element closure means that moves the projecting elements from a fanned out position to a position where they are substantially parallel to the longitudinal axis of the shaft of the medical scoping device. Preferably, the projecting elements closure means is in the form of a sleeve that is capable of being drawn over the projecting elements. Preferably, the projecting elements closure means is provided with a draw string or the like which allows the sleeve to unfurl in a proximal direction.

Preferably, the bases of the moulded projecting elements are raised so that they form a bump or bulge on the outer surface of the elongate tubular member under which is an air pocket. The projecting elements are hinged or moveable about their bases to enable them to be moveable and in one embodiment to flick over beyond a critical point of maximum flexion so that the tips point distally to allow for a smooth removal of the medical device from the body passage and orifice into which the device has been inserted.

Preferably, the bases of the moulded elements are attached at their base to circumferentially positioned cross members. The projecting elements are hinged or moveable about their bases to flick over beyond a critical point of maximum flexion so that the tips point distally to allow for a smooth removal of the medical device from the body passage and orifice into which the device has been inserted.

Preferably, the hinges at the bases of the projecting elements facilitate movement of the projecting elements between a resting position at an acute angle, preferably between 85 to 35° and more preferably about 55 to 75° in addition to a tendency to collapse to the second position i.e. one that is substantially parallel to the horizontal access. The hinges also facilitate a tendency to resist flexion to a point substantially perpendicular to the longitudinal axis (90°) and a tendency to flatten to an obtuse angle i.e. flipping over to about 170-180° upon extubation after a critical angle is exceeded.

Preferably, the hinges maybe of variable stiffness.

Preferably, the bristles are between 2 to 20 mm in length from base to tip and more preferably they are between 4 to 15 mm in length and more preferably still are between 4 to 10 mm in length.

In embodiments of the invention where multiple rings of projecting elements are provided then preferably, the length of the bristles is marginally shorter at either or both the distal and proximal ends of the cover. Thus the central region of the cover comprises bristles of a longer length so that the bristles of the cover when seen in side view are elliptical.

Preferably, the projecting elements that are of a longer length are more flexible and are constructed of a softer material than projecting elements of a shorter length and more preferably still the longer projecting elements are everted.

Preferably, in the embodiments where the projecting elements are in the form of bristles or hairs the diameter of the projecting element is between 0.5 to 3.0 mm and more preferably still is about 1.5 mm.

Preferably, the projecting elements may be either straight or curved. Projecting elements with a slight curve offer the advantage of when they abut or contact the colonic wall there is a tendency to deform, so that the tip of the projecting element bends out rather than pressing into or impinging onto the colonic wall causing trauma. The slight curve reveals the under surface of the projecting elements into the colonic wall, pushing it away and flattening folds as they pass by.

It will be appreciated that the elongate tubular member and the projecting elements are constructed of a suitable biocompatible material so that they are flexible and resiliently deformable, suitable materials include but are not limited to a material selected from the group comprising polymers, plastics, elastomers and rubbers. Suitable examples include polyurethane, polychlorpropene, natural rubber, silicon and silicon elastomeric materials a particularly preferred material is a thermoplastic elastomer for example and without limitation Pebax®.

Preferably, the elongate tubular member and projecting elements are constructed from the same or differing materials, from a manufacturing perspective a cover comprising the same construction material is preferred however it is within the scope of the invention to construct the projecting elements from a different material to the elongate tubular member's main body.

Preferably, the projecting elements in a resting position are acutely angled with respect to the central longitudinal axis of the cover and more preferably the projecting elements are positioned at an angle of between 35° to 85° with respect to a central longitudinal axis of a central line of the cover, more preferably they are angled at about 55° to 75° from the cover's central longitudinal axis.

Preferably, the projecting elements are positioned in rings running circumferentially around the cover and along the length of the cover. Ideally, there is at least one or more rings and more ideally two rings and in other embodiments up to 20 rings. It will be appreciated that the projecting elements may, in some embodiments, be provided as a single ring.

Preferably, each ring comprises between 4 to 16 projecting elements and more preferably between 5 to 10 projecting elements. The rings of projecting elements may be aligned uniformly in parallel descending the length of the cover or they may be off set against one another.

Preferably, the rings of the projecting elements are spaced apart by a distance of between 2.5 cm to 0.5 cm and more preferably still by about 1.5 cm to 0.5 cm.

It will be appreciated that the cover of the present invention may be constructed uniformly, that is to say that the projecting elements may all be of equal diameter, length, number in ring and evenly spaced apart rows of rings in a uniform manner. Alternatively, it is included within the scope of the invention that any one or more of these parameters may comprise a mixture of different parameters, that is to say that the cover may comprise projecting elements of differing diameters, lengths, numbers in rings and the rows of rings may be differentially spaced apart in a non-uniform manner.

Preferably, the cover further comprises an over cuff. The over cuff is placed over the cover of the present invention. In the embodiments of the invention where the cover comprises slits or gaps, the over cuff is also provided with slits or gaps of the same dimensions as that of the cover so that the projecting elements are able to protrude through the aligned slits or gaps.

Preferably, the over cuff is of the same or approximately same length as the cover.

Preferably, the over cuff is constructed of a polycarbonate or the like.

Preferably, the first ring of projecting elements, i.e. the most distal ring, is positioned between 1 to 20 mm from the distal end of the cover and more preferably it is positioned between 5 to 15 mm from the distal end.

Preferably, in the instance of multiple rings the last ring of projecting elements, i.e. the most proximal ring, is positioned between 1.0 cm and 10.0 cm from the proximal end of the cover and more preferably it is positioned between 1.0 cm and 3.0 cm from the proximal end.

Preferably, the cover is provided with one or more apertures positioned at the proximal end of the cover. The apertures are provided so that they may slot over the securing means of an applicator casing thereby holding the cover in position for receiving an enteroscope or endoscope into the hollow body of the elongate tubular member. More preferably, the cover comprises at least four apertures evenly spaced apart for securing the cover to the applicator casing prior to insertion of the scope into the cover.

Preferably, the cover further comprises a viewing means mounted at its distal end. The viewing means is preferably a disposable transparent tubular open ended cap and may be in the form of a plastic or Perspex® cap attachment which can facilitate maintaining image focus and correct depth of field. The addition of a transparent plastic open ended cap can advantageously permit entry into the ileum.

Preferably, the outer surface of the cover (i.e. the surface of the cover that is, in use, in contact with the patient's body cavity) is coated with a lubricating agent that maybe a hydrophobic or hydrophilic agent. Suitable hydrophilic agents include, but are not limited to, hydrogel polymers such as poly(2-hydroxyethyl methacrylate) (PHEMA) and ComfortCoat®, suitable hydrophobic agents include, but are not limited to, silicone, glycerine, olive oil, castor oil, chlorotrifluoroethylene (CTFE oil) and polyphenyl ethers or a mixture thereof.

Preferably, the lubricating agent is sprayed or brushed onto the outer surface of the cover and more preferably still, is coated only onto the distal end of the cover so that only the outer surface of distal end of the cover is coated leaving the proximal surface and under surface of projecting elements free of the lubricating agent thereby providing greater purchase on the surface of the body passage during extubation facing aspects e Preferably, the cover is detachable or removable from the endoscope/enteroscope. In use, the cover of the present invention is placed about the medical device shortly before insertion into the patient under investigation and is removed from the medical device once the examination/procedure has been completed. The cover of the present invention may then be disposed of.

Preferably, the cover of the present invention is provided with the projecting elements along its length and especially when in position on a medical scoping device at its distal end. The main difficulty with performing colonoscopy is the anatomy. Some lengths of bowel are attached to loose mesentery rendering them mobile and subject to looping whilst other parts are fixed, often causing a sharp change of direction which leads to greater friction when trying to advance around the bend. Furthermore, depending upon the tightness of the bend, the tip of the colonoscope (or the flexed knuckle that has been induced at the end of the instrument to steer round the bend) abuts the side wall of the bend so that forward momentum induced by the endoscopist is directed in the opposite direction to the one desired preventing any advance and leading to trauma at the point of contact and increased looping in the mobile segment. Because there is an angle to be negotiated at these fixed points, forward vision may be lost as well.

Until the acute bend has been negotiated pushing the colonoscope forward leads to the development of a loop in the mobile segment. This in turn creates tension on the mesentery causing pain, slowing the heart rate and lowering the blood pressure. Further attempts to "push round the loop" can lead to damage of the bowel both in the looped segment and at the tip of the colonoscope if its end is hard against the wall of the bowel. Advantageously, the projecting elements of the cover of the present invention provide an ease of movement around the relevant regions thereby reducing tension between the bowel surface and the instrument and allowing for the colon to be concertinaed behind the distal end.

In the present invention the projecting elements are designed to open out when the scope is withdrawn from a patient and this creates a fan or spread of projecting elements that gently support the wall of the body passage and especially the colon. When the colon is tortuous, withdrawing the colonoscope draws the colon back, opening up the path ahead. Forward motion simply causes the hairs to collapse against the side of the sleeve so that they are in the so called second position and are substantially parallel to the longitudinal central axis of the scope accordingly the scope can be advanced without hindrance. In practice the technique of forward advancement and drawing back allows for rapid concertinaing of the colon behind the cover and also advantageously opens the way ahead so reducing loss of vision in the procedure especially when looping. Furthermore, it enables rapid advancement through a tortuous colon without losing position.

As regards the suctioning effect or "wrap around" which is an entirely new concept in the field, suction of air draws the colonic wall into close apposition to the colonoscope wall, wrapping it around the cover and in between the projecting elements into the spaces therebetween. This in turn increases the backward friction and allows the colonoscope to be withdrawn, shortening and telescoping the proximal colon over the shaft whilst not allowing the distal end or tip to slip backwards.

Yet further advantages of the cover of the present invention include close approximation of the colonic wall to the projecting elements or hairs enhancing tip grip, maintenance of distal tip position when reducing a proximal loop, straightening out the distal bowel tortuosity.

It will be appreciated that the cover of the present invention may be used in conjunction with existing scopes and that no special modifications to scopes currently used in practise is required.

In one aspect of the invention the applicator comprises two complimentary casings that engage together to form a hollow shell, the engaging means may be in the form of snap-fit male-female elements, clips or locks or the like the specifics of which are not intended to limit the scope of the invention.

Preferably, the securing means of the applicator comprise rod like projections that engage with apertures provided at the proximal end of the cover, the apertures in the cover are sized and shaped so as to accommodate the rods therein. Thus, the apertures of the cover are placed over the rods to secure the cover within the casing or shell and then the medical device scope is inserted into the hollow space of the elongate tubular member. Preferably, the number of securing means (rods and apertures) are commensurate on the applicator and cover.

Preferably, the applicator may further include an end cap that is slotted into position and held secure so that when the medical scoping device is inserted into the application its distal end abuts and engages with the end cap.

Also included within the scope of the invention is a kit of parts comprising at least one cover having all the features as herein before described, a medical scoping device that includes an air suction means, an applicator for placing the cover about the scope and optionally a transparent open-ended cap held either within the applicator or attached to the cover itself.

It will be appreciated that the cover of the present invention can be constructed with various diameters so that it may be used to fit over the shaft of existing medical scoping devices. For example, paediatric scoping devices comprise shaft diameters of around 11 mm whereas an adult scoping device shaft diameter is in the region of 12 mm, the cover of the present invention may be constructed with suitable diameters according to a user's requirements.

The invention will now be described with reference to the Figures.

Figure 9B:
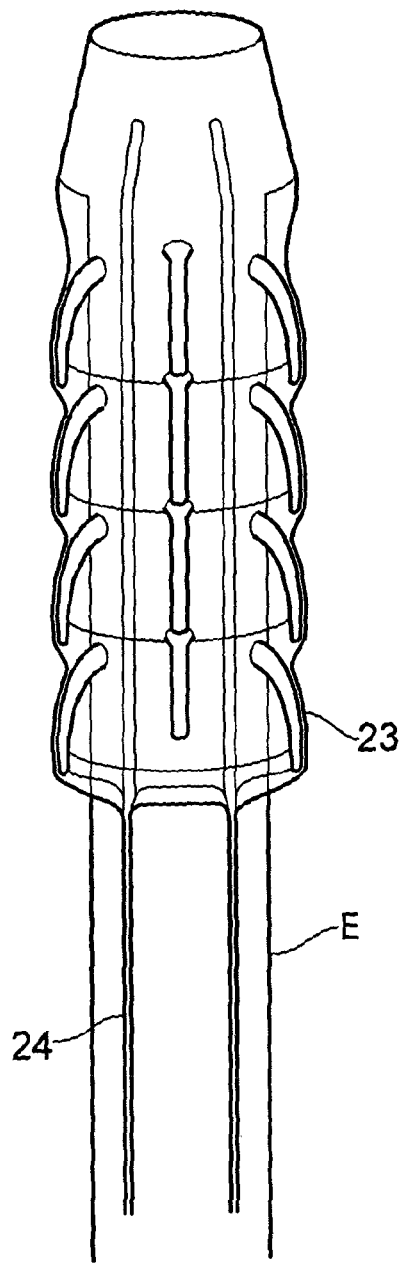
FIG. 9A shows the cover of the present invention having one embodiment of the projecting elements closing means and FIG. 9B shows a cover having flattened projecting elements.

FIG. 1 shows a cover (1) according to the present invention, the cover comprises a number of projecting elements (2) in the form of bristles, moulded at an acute angle with respect to the longitudinal axis of the cover to the outer surface (3) of the elongate tubular member. FIG. 1 shows the projecting elements in their resting position and the tips pointing towards the proximal end (6). The projecting elements (2) are moulded at their base to form a raised portion or bump (4). A small air pocket is formed beneath the raised portion or bump (4) on the inner surface (7) of the cover which allows for flexibility of the projecting elements about their base in use and especially when negotiating the confines of a body passage. As described herein before the projecting elements are angled, at rest in the so called first position, to around 45° to 65° towards the proximal end (6) of the cover and with respect to a central longitudinal axis of the cover and, in a forward or distal movement within a body passage once the endoscope or enteroscope has been inserted into the hollow (8) of the cover, the projecting elements are flattened so as to be approximately parallel to the said longitudinal axis with the projecting elements tips pointing towards the proximal end (6). This is the second position. The projecting elements are fanned out or expanded into a third position when the covered scope is withdrawn in a proximal movement. During this reverse movement the endoscopist can apply the air suction means to withdraw air from the body passage causing the body passage wall to partially collapse about the projecting elements (2) and be drawn into the spaces (3) between the individual projecting elements and the spaces between rings and rows of rings of projecting elements. In this way the wall of the body passage is gripped and wrapped around the cover, if further forward or distal movement is applied the body passage wall remains gripped by the projecting elements and effectively bunches up or concertinas in the proximal area thereby allowing the distal end to move forward and overcome the looping or bend obstacle. In some embodiments of the invention the projecting elements (2) are capable of flicking or flipping over past the critical point of maximum inflexion at 90° so that the tips point towards the distal end (5) in a so called fourth position, making withdrawal of the device through the relevant orifice more comfortable for the patient. Alternatively they may be flattened against the cover main body as depicted in FIG. 9B as described herein after. In use, in preliminary trials endoscopists have reported that the cover of the invention remains in position on the flexible medical scoping device shaft and that the projecting elements do not impede the periphery of the visual field.

Figure 8A:
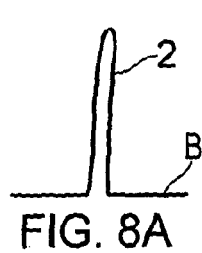
FIG. 8A-E shows different embodiments of the projecting elements.
Figure 8B:
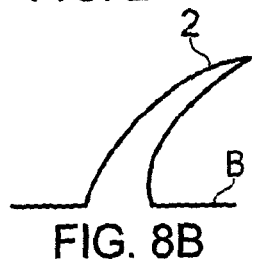
Figure 8C:
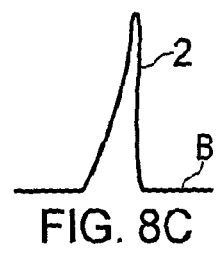
Figure 8D:
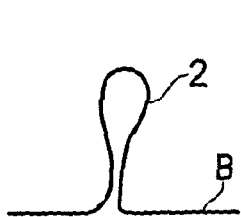
Figure 8E:
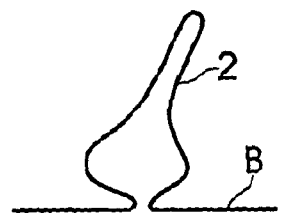

The projecting elements may be in form of bristles (FIG. 8A), fins or paddles (FIG. 8B), cones (FIG. 8C), bulbs, stalks or buds (FIG. 8D) or any other flexible projection (FIG. 8E).

Figure 2:
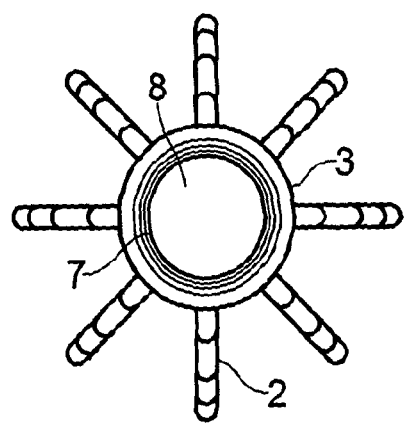
FIG. 2 shows a transverse section through the cover of FIG. 1.

The projecting elements are provided in rings, typically of about 1 to 10 rings and more typically of two rings in uniform circumferential formation and evenly spaced apart with projecting elements being of a marginally shorter length in the first (distal end (5)) and last (proximal end (6)) rows. At the proximal end (6) the cover is provided with several apertures (16) which are capable of fitting over rods provided on the applicator. FIG. 2 shows a transverse section through the cover that has bristle type projecting elements.

Figure 3:
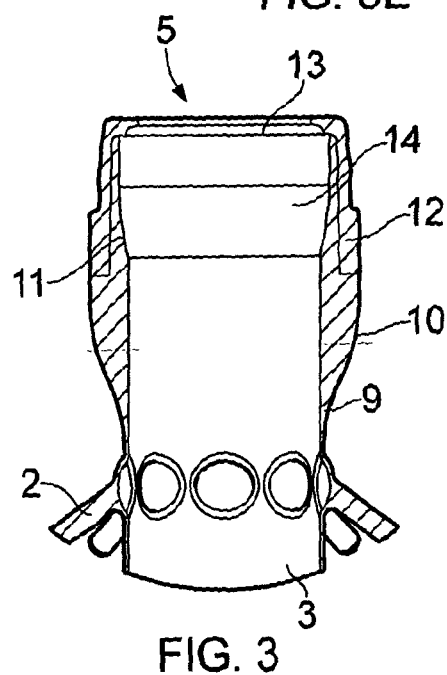
FIG. 3 shows in detail a longitudinal section of the distal end of the cover of FIG. 1.

With regard to FIG. 3, the distal end (5) of the cover is seen in greater detail. The distal end comprises a head (14) and a profiled end region (9, 10) over which a transparent cap (13) may be placed and held in position by clips (11, 12) or the like. This distal region is the end that is furthest in the patient and provides the light and lens through which the endoscopist can observe the body passage. In some embodiments of the invention the cap (13) is provided with the cover or may be placed in the applicator and the scope is inserted through the cover and caused to engage with the cap in situ. The end cap is an optional additional feature which can be provided if desired with either the cover or the applicator.

Figure 4:
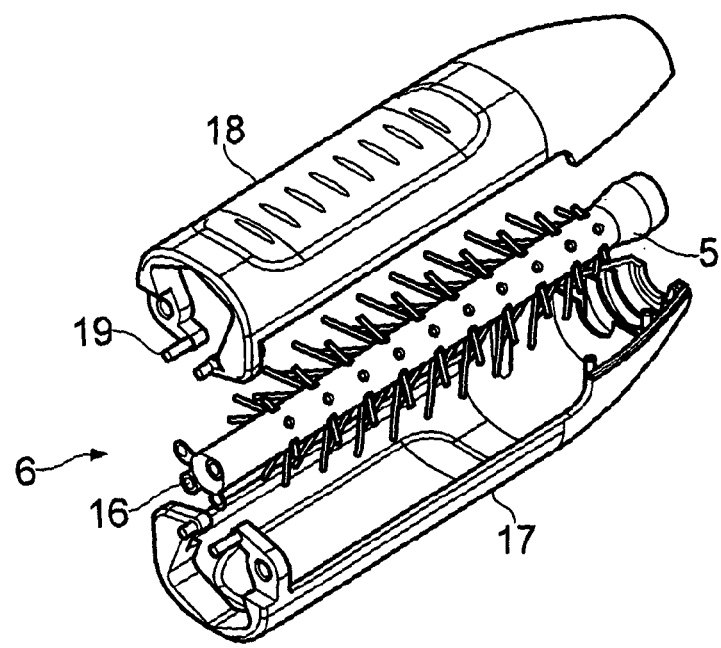
FIG. 4 shows a disassembled applicator and cover.
Figure 5:
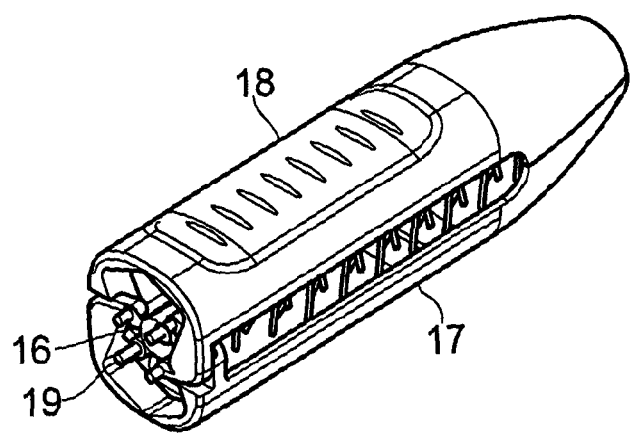
FIG. 5 shows an assembled applicator and cover.

In order to place the cover about an enteroscope or endoscope the cover is held in place within an applicator comprising a pair of casings (17, 18). FIG. 4 shows a disassembled applicator and the securing means (19) of the casings (17, 18) in the form of rods which are inserted into apertures (16) of the proximal end of the cover. Although not shown in FIG. 4 an end cap can be held in place at the distal end. In FIG. 5, the casings are fitted together by any suitable means and the cover held in position within the shell or casing. In order to fit the cover about a scope, the scope is inserted into the hollow (8) and pushed up into the casing towards the distal end (5) whilst the cover is secured about its proximal end (5) by means (16, 19). FIG. 6A shows a top view of an assembled casing and FIG. 6B shows a side view with the cover in place inside, FIG. 6C shows a top view of a disassembled applicator and cover, FIG. 6D shows a proximal end view with the apertures of the cover over the rods stretching the cover to form an interior space 20 through which the scope is inserted and FIG. 6E shows a distal end view with the viewing hole which may also include the end cap. In one aspect of the invention there is provided a kit of parts which may optionally include a viewing means attachment (20) optionally provided with a portal (21) for removing under suction any excess fluid (FIG. 7).

Figure 9A:
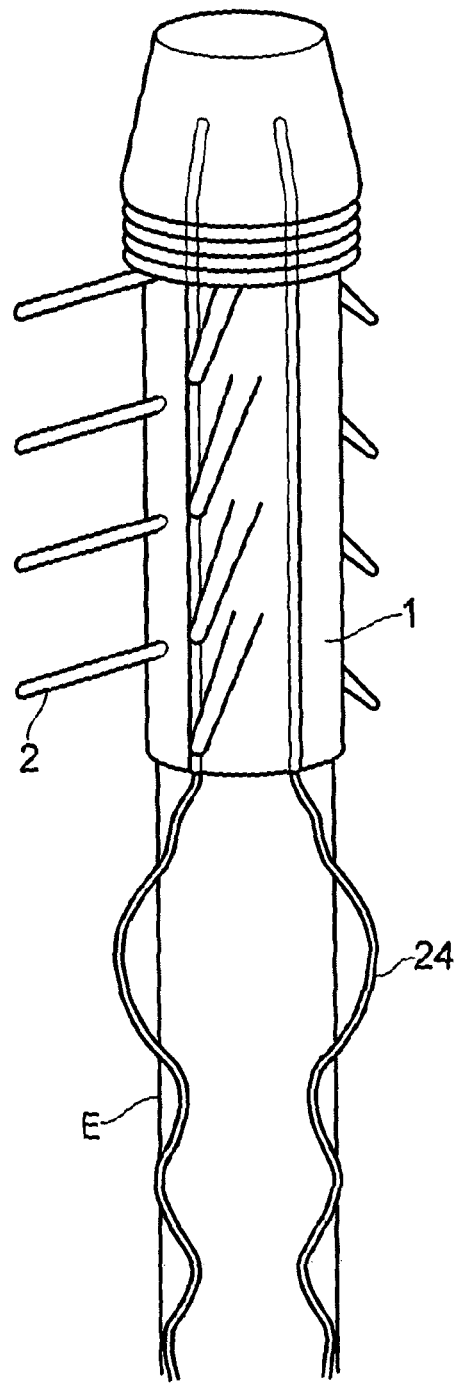

As mentioned herein before, in some embodiments of the invention the projecting elements are not configured to adopt the fourth position where the tip ends are pointed in a distal direction following a flip over past the critical point at maximum inflexion. In such embodiments, the cover is provided with a projecting element closure means (23) typically in the form of a sleeve (FIGS. 9A and 9B). To close the projecting elements, in order that the scoping medical device can be comfortably withdrawn out of the orifice into which it was inserted, the projecting elements closure means is pulled over the projecting elements by a cord or line or string (24) so that sleeve (23) unfurls in a proximal direction over the projecting elements (2) thereby flattening them against the scope shaft (E). Once flattened (FIG. 9B) the scope can be withdrawn from the patient.

Figure 10A:
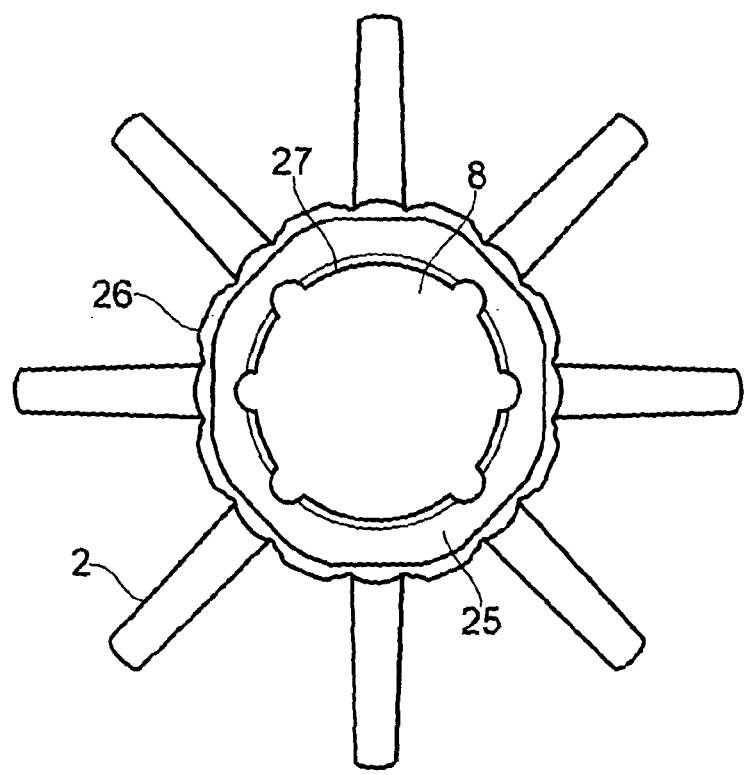
FIG. 10A shows a top plan view and FIG. 10B shows an underside plan view.
Figure 10B:
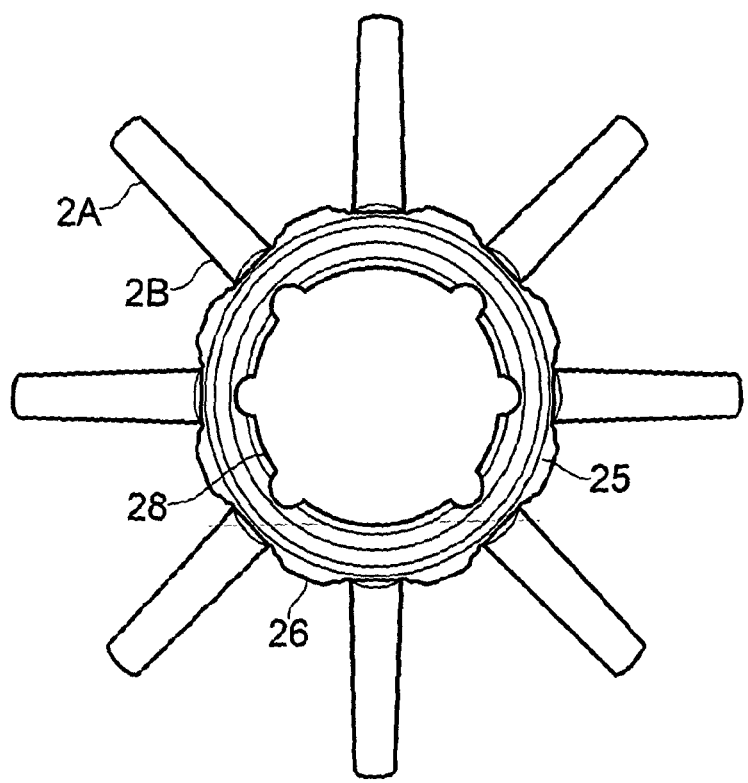
Figure 11A:
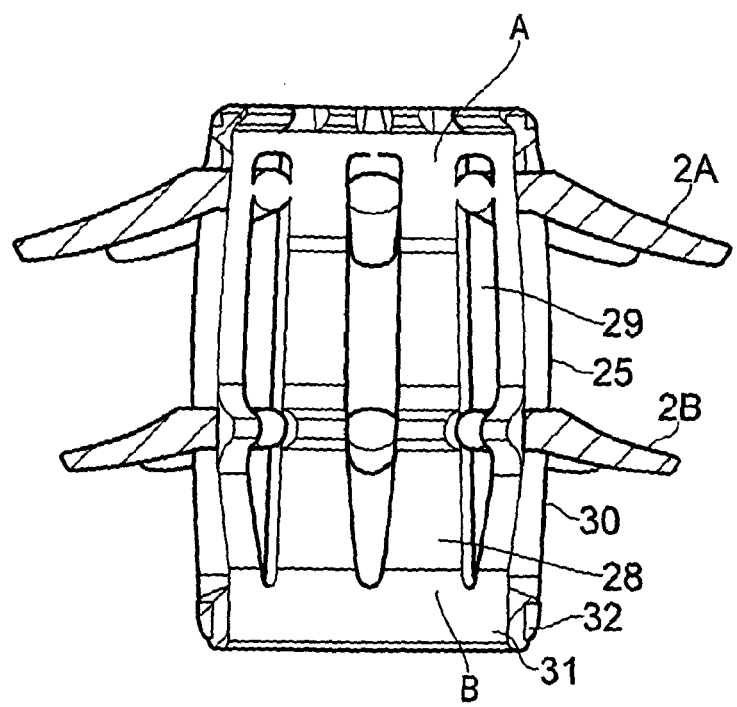
FIG. 11A shows a transverse through section.
Figure 11C:
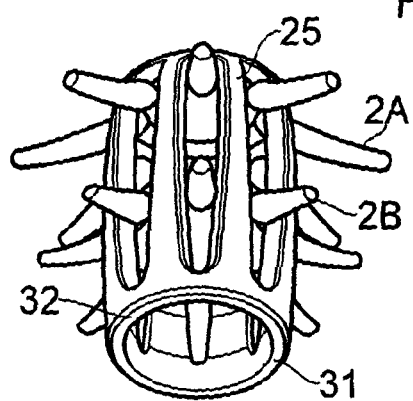
FIG. 11B shows a front view and FIGS. 11C and 11D show bottom and top side angled views.
Figure 11B:
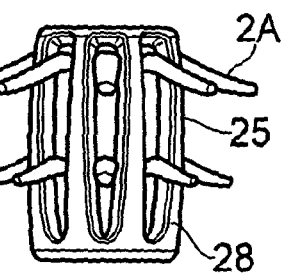
Figure 11D:
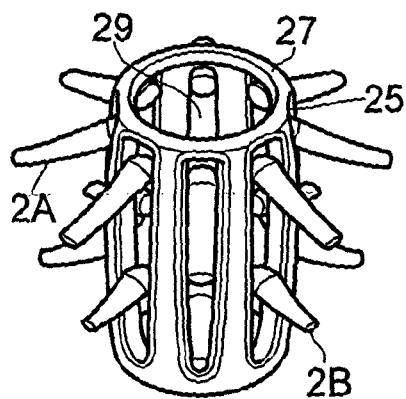
Figure 11E:
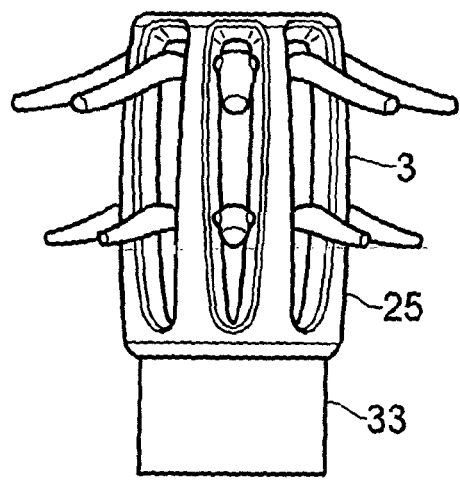
FIG. 11E shows the cover including the over cuff placed over the distal end of a medical scoping device.

In an alternative embodiment of the invention the cover is provided with slits or gaps (28) running in a longitudinal direction and between the distal (A) and proximal (B) regions of the cover, in this embodiment the cover is also provided with an over cuff (25). The over cuff itself is also provided with slits or gaps (30) between its proximal and distal ends that are of approximately commensurate dimensions as the slits or gaps in the cover so that, when the over cuff is placed over the cover, the slits or gaps in both the cover and over cuff are aligned, providing continuous spaces (29) through both items whilst at each of the distal (A) and proximal (B) ends the cover and over-cuff have continuous rings (31 and 32). The slits or gaps through which projecting elements can protrude are spaces (29) defined by adjacent strips of the cover (28) and over cuff (30) between the proximal and distal ends. FIG. 10A shows a plan view of a cover and over cuff (25). The over cuff has a snug fit over the cover and is typically constructed of a polycarbonate or other plastics material, projecting elements (2) protrude outwardly between strips (26) of the over cuff and at the distal tip the over cuff it marginally overlaps the cover providing a rim (27) around hollow (8). At the proximal end of the cover and over cuff (FIG. 10B), the differential lengths of projecting elements can be seen, the longer elements (2A) at the distal end project beyond the shorter elements (2B) at the proximal end by between 2-4 mm. Each projecting element protrudes between the slits or gaps (29) defined by the strips (26 and 28) of the over cuff and cover respectively. FIGS. 11A through to 11D show various views of the cover and over-cuff of the present invention and FIG. 11E shows the cover and over cuff arrangement when placed over the distal end shaft (33) of a medical scoping device.

Figure 12A:
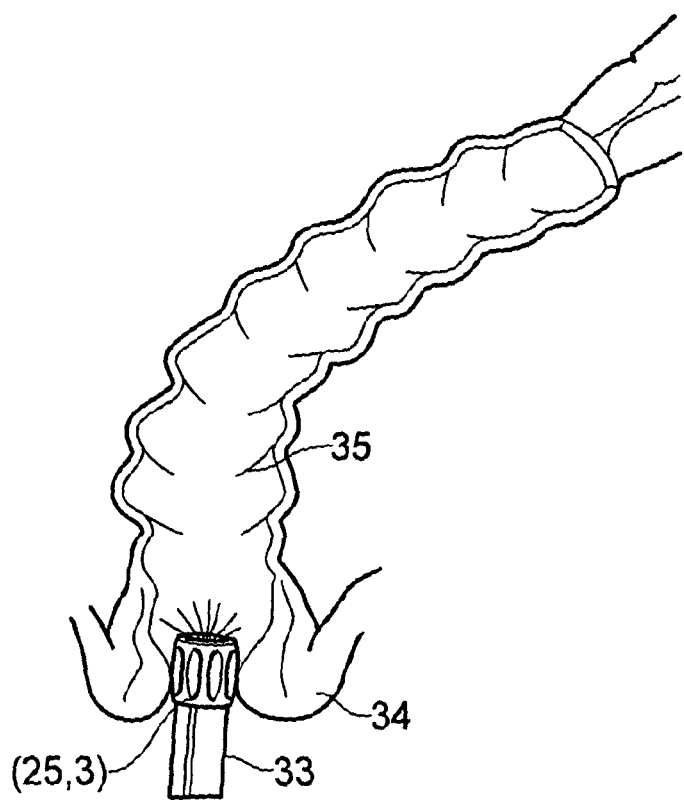
FIG. 12A shows insertion of the scoping device and cover via the anus into the colon of an individual undergoing an endoscopic procedure.
Figure 12B:
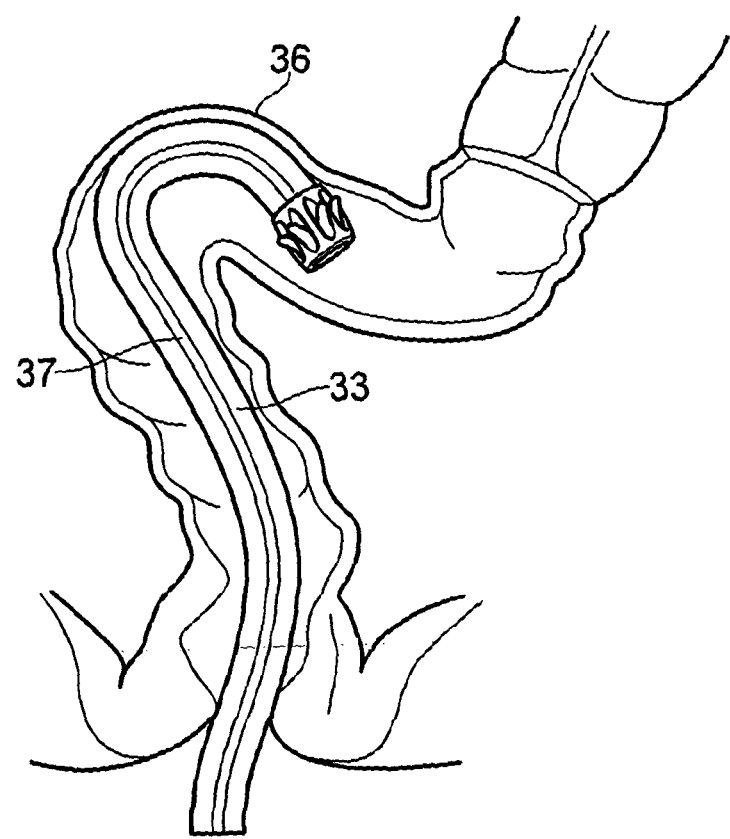
FIG. 12B shows forward passage along the colon.

In use, as depicted in the series of FIGS. 12A to 12D, the medical scoping device distal tip with the cover and over cuff (3, 25) is inserted via the anus (34) into the colon of an individual under investigation. On inserting the medical scoping device, cover and over cuff into the patient the projecting elements are moved from an at rest position, referred herein before as the first position to a second position where they are flattened towards the medical scoping device shaft the so called second position (FIG. 12A). The distal end tip of the medical scoping comprises a channel (37) through which a light source, image relaying mean and air suction is supplied. During intubation, the projecting elements are designed to collapse into the device during insertion through the anus. This exposes the smooth low friction surface of the cover and over cuff to the mucosa to aid intubation.

Negotiating the sigmoid loop is improved by at least one or two rows of projecting elements that offer different functions depending on the requirement of the endoscopist. The longer distal hairs are soft and slightly everted so that they gently grip the mucosa to maintain tip position when the endoscope is straightened "soft grip". When complex loops form and there is a need for stronger grip at the tip to enable their reduction, conventional suction draws the colon close to the surface of the cover creating "wrap around". The colonic mucosa envelopes the proximal shorter projecting elements providing a tight hold while the colonoscope is shortened to enable the bowel to concertina over the shaft of the endoscope without tip slide-back. "Wrap around" avoids the use of acute tip deflection to maintain tip position and reduces the need to torque. Endoscopists report that both techniques are intuitive and simple to perform. Straightening a looped endoscope without losing tip position or vision advantageously potentially reduces time to caecum and patient discomfort. In the course of preliminary trials with the device of the present invention, endoscopists have reported no impediment to intubation and a greater amount of exposure of mucosa in the sigmoid area during withdrawal.

Figures 12C, 12D:
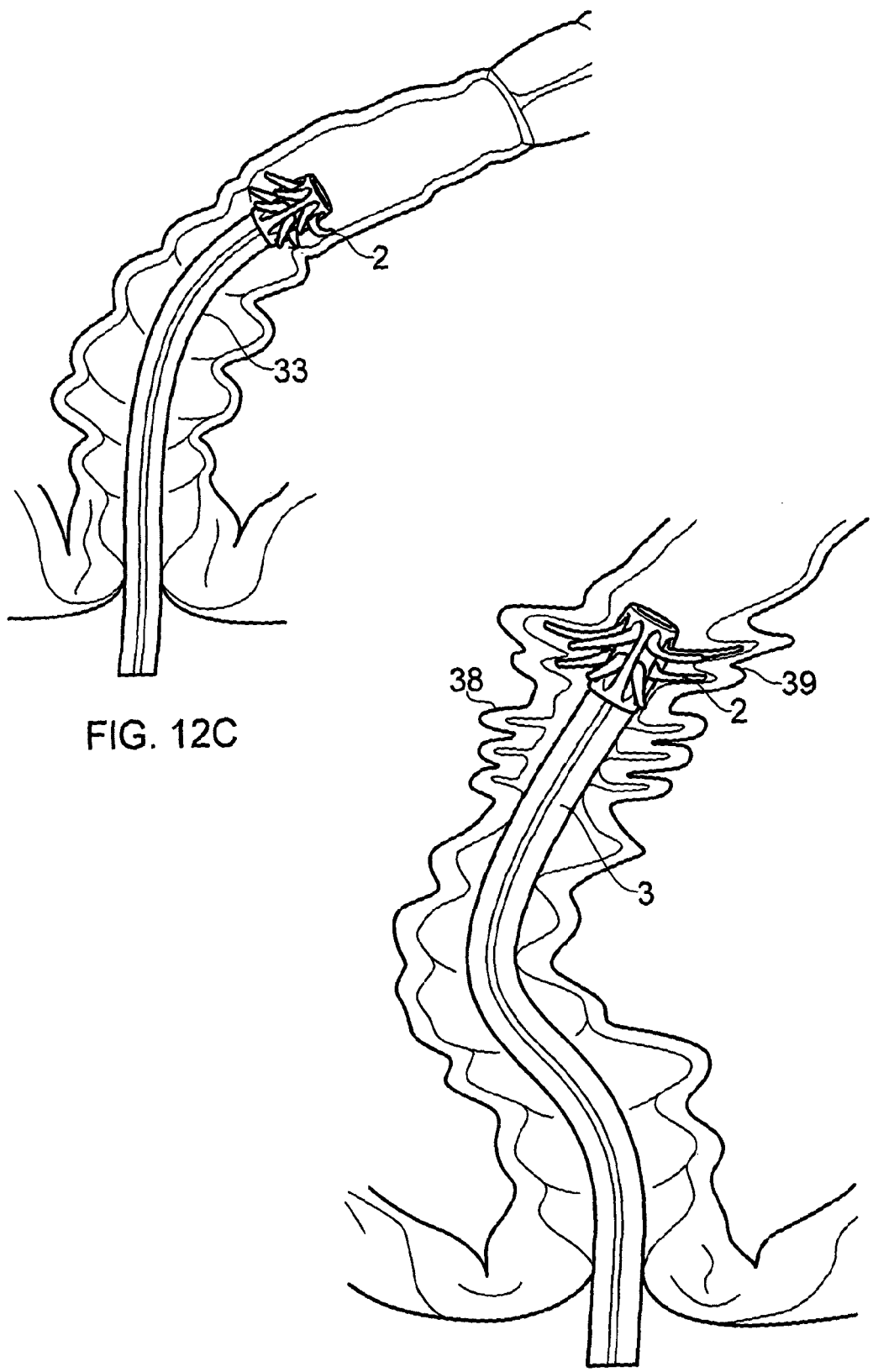
FIG. 12C shows controlled withdrawal, flattening of the colonic wall and improved visualisation.
FIG. 12D shows air suction causing the colon wall to collapse or wrap around the device and to grip the cover and device.

The flexible shaft (33) of the medical scoping device is advanced in a distal direction through the colon towards the bend or loop region (36) of the of the colon (FIG. 12B) whilst insufflating the colon immediately forwards of the distal tip. The projecting elements once passed the anus revert to their resting first position. As the scope passes further up the colon and encounters the loop region the projecting elements engage with the colon wall in a soft grip (third position where the projecting elements fan out and the endoscopist can perform a controlled proximal withdrawal flattening the colonic folds for good visualisation (FIG. 12C). As regards improved visualisation, the distal row of longer projecting elements is designed to open the colonic lumen for close inspection. Viewing the proximal surface of the colonic folds is difficult and time consuming. The projecting elements of the cover of the present invention act to gently open and flatten the colonic folds for inspection during withdrawal, endoscopists report that the cover of the present invention provides distinct improvements. Improved visualisation is important for identifying small pre-malignant and malignant lesions that might be tucked out of sight when performing conventional endoscopy. Visualisation is further enhanced when using the cover of the present invention, especially with wide vision endoscopes.

As mentioned herein before two of the significant disadvantages associated with colonoscopy and scoping procedures is firstly that the natural folds of the colon wall hamper the colonoscopist's ability to visualise the entire surface of the mucosa and secondly in maintaining and controlling position of the distal tip during the procedure. These two difficulties are resolved as follows:

For improved visualisation, the projecting elements gently open the lumen and evert thereby flattening the colonic folds for inspection during withdrawal. Visualisation is further enhanced as the colonic folds slowly revert to their normal anatomical position permitting light to play across the mucosa, thus enabling careful visualisation of the surface of the mucosa that was hitherto hidden or difficult to view.

As regards, tip position control, the projecting elements of the device gently stabilise the tip of the scoping device within the lumen of the colon or small intestine immediately prior to and during therapeutic procedures. This has the advantage of permitting the endoscopist the reassurance that the tip will remain in position from the stage of visualising a lesion or polyp until completion of the therapeutic procedure.

In use, the distal row of the projecting elements are designed to flare outwards on withdrawal. They keep the instrument tip in the central part of the bowel lumen as the instrument moves backwards, gently holding the mucosa to prevent the tip from flipping backwards, they maintain position during therapy and improve all-round visualisation. During extubation they evert the folds enabling their proximal surface to be viewed.

In order to negotiate the loop or bend the endoscopist can apply air suction so that the colon wall (38) collapses onto the shaft (3) and into the spaces between adjacent rings of projecting elements (39), the projecting elements still being in the third position (FIG. 12D). The colon wall concertinas about the shaft (3) and the endoscopist can then cease suction so that the colon wall straightens and the scope can be further advanced.

On withdrawing the scope especially through the anus the projecting elements can flip over to the fourth position so that the scope can be comfortably withdrawn. During controlled tip withdrawal, the cover of the present invention is designed to provide controlled extubation. During conventional withdrawal there is a tendency for the colonoscope tip suddenly to slip backwards. This happens especially when passing a bend or flexure and the "missed" area then has to be re-intubated, sometimes with the creation of a painful loop. The long, soft, distal projecting elements of the present invention prevent sudden tip slippage and hold the tip in the centre of the colonic lumen providing both control and good visualisation as the endoscope is withdrawn.

The invention claimed is:

1. A method of endoscopic visualization of a bowel and/or small intestine, the method comprising:

inserting a medical scoping device shaft having an air suction conduit for removing air from a body passage into the bowel or small intestine of a patient under investigation, the medical scoping device further comprising a cover releasably attached to the medical scoping device shaft and covering at least a part of the shaft at its distal end, wherein the cover includes a member having an inner surface for gripping the shaft and an outer surface from which a plurality of projecting elements project radially outwardly;

advancing the medical scoping device in the direction of its distal end within the patient's bowel or small intestine, wherein the projecting elements deflect to a first radially inward position to facilitate advancing the medical scoping device;

partially withdrawing the medical scoping device toward its proximal end, such withdrawal causing the projecting elements to deflect to a second radially outward position in which at least some tips of the projecting elements extend distally further than a distal end of the cover and the distal end of the medical scoping device in response to contact with a lumen wall to dilate a lumen of the bowel or small intestine while holding the medical scoping device in position for visualization of the lumen and to evert and engage colonic folds that are more distal than the distal end of the cover and the medical scoping device whereby visualization is allowed as the colonic folds revert to their normal anatomical position permitting a light from the medical scoping device to emit across a mucosa of the bowel or small intestine providing visualization of at least a portion of a surface of the mucosa; and withdrawing the medical scoping device wherein the projecting elements deflect so that the tips of the projecting elements extend distally further than the distal end of the cover and the distal end of the medical scoping device to facilitate withdrawal of the medical scoping device.

2. The method of claim 1, wherein the projecting elements are substantially perpendicular to the longitudinal axis of the shaft of the medical scoping device in the second position.

3. The method of claim 1, wherein, in response to when the projecting elements dilate the lumen and evert, at least some of the projecting elements can flatten colonic folds in the bowel or small intestine for inspection in the second position.

4. The method of claim 1, wherein the projecting elements comprise bristles, spikes, spines, fins, wedges, paddles or cones that are arranged to extend radially outwardly from the outer surface of the medical scoping device shaft.

5. The method of claim 1, wherein the projecting elements comprise a biocompatible flexible material selected from the group consisting of a polymer, plastic, elastomer, silicon, a silicon elastomeric material and a rubber, and combinations thereof.

6. The method of claim 1, wherein the cover further comprises a viewing device at the distal end.

7. The method of claim 1, wherein the projecting elements deflect at a critical point of maximum flexion so that at least some of the tips of the projecting elements point towards and extend beyond the distal end of the medical scoping device during the partially withdrawing and/or withdrawing steps.

8. A method of endoscopic visualization of a bowel and/or small intestine, the method comprising:

inserting a medical scoping device shaft having air suction for removing air from a body passage into the bowel or small intestine of a patient under investigation, the medical scoping device further comprising a cover releasably attached to the medical scoping device shaft and covering at least a part of the shaft at its distal end, wherein the cover grips the shaft and comprises a plurality of projecting elements that project radially outwardly;

advancing the medical scoping device in the direction of its distal end within a lumen of the patient's bowel or small intestine or bowel and small intestine, wherein the projecting elements deflect to a first radially inward position to facilitate advancing the medical scoping device;

partially withdrawing the medical scoping device toward its proximal end, such withdrawal causing the projecting elements to deflect to a second radially outward position at which at least some tips of the projecting elements extend distally further than a distal end of the cover and the distal end of the medical scoping device in response to contact with a lumen wall to dilate the lumen while holding the medical scoping device in position for visualization of the lumen and to evert and engage colonic folds that are more distal than the distal end of the cover and the medical scoping device whereby visualization is allowed as the colonic folds revert to their normal anatomical position permitting a light from the medical scoping device to emit across a mucosa of the lumen providing visualization of at least a portion of a surface of the mucosa; and withdrawing the medical scoping device wherein the projecting elements deflect so that at least some of the tips of the projecting elements extend distally further than the distal end of the cover and the distal end of the medical scoping device to facilitate withdrawal of the medical scoping device.

9. The method of claim 8, wherein, in response to when the projecting elements dilate the lumen and evert, at least some of the projecting elements that extend beyond the distal end of the cover and the medical scoping device flatten colonic folds in the bowel or small intestine for inspection in the second position.

* * * * *